(12) United States Patent
Pillai

(10) Patent No.: US 11,478,251 B2
(45) Date of Patent: Oct. 25, 2022

(54) ANEURYSM OCCLUDER

(71) Applicant: Jayandiran Pillai, Johannesburg (ZA)

(72) Inventor: Jayandiran Pillai, Johannesburg (ZA)

( * ) Notice: Subject to any disclaimer, the term of this patent is extended or adjusted under 35 U.S.C. 154(b) by 0 days.

(21) Appl. No.: 15/772,373

(22) PCT Filed: Oct. 27, 2016

(86) PCT No.: PCT/IB2016/056474
§ 371 (c)(1),
(2) Date: Apr. 30, 2018

(87) PCT Pub. No.: WO2017/072695
PCT Pub. Date: May 4, 2017

(65) Prior Publication Data
US 2018/0317925 A1 Nov. 8, 2018

(51) Int. Cl.
*A61B 17/17* (2006.01)
*A61B 5/0215* (2006.01)
*A61B 5/00* (2006.01)
*A61B 17/12* (2006.01)
*A61B 5/07* (2006.01)
*A61B 17/00* (2006.01)

(52) U.S. Cl.
CPC ........ *A61B 17/1219* (2013.01); *A61B 5/0215* (2013.01); *A61B 5/076* (2013.01); *A61B 5/686* (2013.01); *A61B 17/12118* (2013.01); *A61B 17/12177* (2013.01); *A61B 5/0031* (2013.01); *A61B 5/6851* (2013.01); *A61B 2017/00893* (2013.01); *A61B 2017/00898* (2013.01); *A61B 2560/066* (2013.01)

(58) Field of Classification Search
CPC ... A61B 17/1219; A61B 5/076; A61B 5/0215; A61B 5/686; A61B 17/12177; A61B 17/12118; A61B 5/6851; A61B 5/0031; A61B 2560/066; A61B 2017/00898; A61B 2017/00893
See application file for complete search history.

(56) References Cited

U.S. PATENT DOCUMENTS 4,705,517 A * 11/1987 DiPisa, Jr. ................ A61F 2/95
  623/1.25
6,168,622 B1 * 1/2001 Mazzocchi ........ A61B 17/0057
  606/200

(Continued)

FOREIGN PATENT DOCUMENTS

WO  WO 2007/006139  1/2007
WO  WO 2013/005195  1/2013
WO  WO 2015/105459  7/2015

OTHER PUBLICATIONS

International Search Report and Written Opinion for PCT/IB2016/056474 dated Jan. 31, 2017 (8 pages).

*Primary Examiner* — Julian W Woo
(74) *Attorney, Agent, or Firm* — Sheppard Mullin Richter & Hampton LLP

(57) ABSTRACT

This invention relates to an aneurysm occluder, and more particularly but not exclusively, to an endovascular aneurysm occluder that can be inserted into an aneurysm cavity by using endovascular surgical procedures. The aneurysm occluder has a deformable housing and an absorber or material that causes blood clotting made of an absorbent material in or attached to the housing.

20 Claims, 4 Drawing Sheets

(56) References Cited

U.S. PATENT DOCUMENTS

| | | | | |
|---|---|---|---|---|
| 6,855,154 | B2 * | 2/2005 | Abdel-Gawwad | ............................ A61B 17/12022 606/200 |
| 7,769,420 | B2 * | 8/2010 | Silver | ................... A61B 5/0031 600/300 |
| 8,317,823 | B2 * | 11/2012 | Pavcnik | ............ A61B 17/12022 606/213 |
| 8,434,490 | B2 * | 5/2013 | Swann | .................... A61B 6/485 128/831 |
| 8,974,487 | B2 * | 3/2015 | Connor | ............ A61B 17/12022 606/198 |
| 9,078,658 | B2 * | 7/2015 | Hewitt | ............. A61B 17/12113 |
| 9,655,602 | B2 * | 5/2017 | Ginn | ................... A61B 17/0057 |
| 9,713,549 | B2 * | 7/2017 | Callister | .................... A61F 6/22 |
| 2011/0230952 | A1 | 9/2011 | Kassab et al. | |

\* cited by examiner

ANEURYSM OCCLUDER

CROSS REFERENCE TO RELATED APPLICATIONS

This application is a U.S. National Stage Application under 35 U.S.C. 371 of International Application No. PCT/IB2016/056474 filed Oct. 27, 2016, which application claims priority to South Africa Application No. 2015/02866, filed Oct. 28, 2015, the contents of which are hereby incorporated by reference in their entirety into the present disclosure.

FIELD OF THE INVENTION

This invention relates to an aneurysm occluder, and more particularly but not exclusively, to an endovascular aneurysm occluder that can be inserted into an aneurysm cavity by using endovascular surgical procedures.

BACKGROUND TO THE INVENTION

An aneurysm is an excessive swelling of a wall segment of an artery and occurs when a wall segment of an artery weakens. Blood pressure in the artery creates the swelling at the weakened wall section. The swelling is commonly referred to as an aneurysm cavity or aneurysm sac. As the size of the aneurysm increases, the risk of rupture increases. A rupture can cause internal bleeding which may result in severe complications and even death.

Endovascular Aneurysm Repair or Endovascular Aortic Repair ("EVAR") is a corrective surgical procedure to repair an aneurysm of the aorta (abdominal or thoracic). The procedure involves insertion of a vascular prosthesis, commonly referred to as a stent graft or graft device. The graft device is tubular and provides an artificial lumen for blood to flow, replacing, or inside, the damaged artery, thereby immediately taking pressure off of the damaged portion of the blood vessel. The procedure is performed percutaneously by, for example, making two small incisions in the groin to expose the femoral arteries and feeding a synthetic stent graft through these arteries, with catheters and guidewires, until the stent graft is positioned. The damaged part of the blood vessel is internally lined by the stent graft and the stent graft attaches, by radial force at either end to the normal, healthy portions of proximal and distal arteries.

The vascular prosthesis must be attached to the blood vessel in such a way that there is a strong, tight seal around the normal, healthy proximal and distal artery so that blood will not escape into the aneurysm sac. In practice, it is often difficult to attach the stent graft to the ends of the blood vessel in such a way that there is a permanent strong, tight seal between the proximal and distal artery and opposing ends of the stent graft and, as a result, blood flow into the aneurysm sac ("endoleak") may occur. An endoleak may occur in up to 20% of all cases and is considered to be a failure of treatment and may be life-threatening.

Endoleak can be treated in a variety of ways. One way to treat endoleak is by open surgical repair and complete replacement of the stent graft. Open surgical repair and the insertion of a new graft carry a high operative mortality rate. Inducing thrombosis is often a successful alternative way of treating the endoleak.

Thrombosis can be induced by injecting a liquid embolic agent, containing a biocompatible polymer, into the endoleak sac. Thrombosis can also be induced in aneurysms by a procedure called endovascular coiling. Endovascular coiling involves packing platinum coils into the aneurysm sac, through a catheter, to restrict blood circulation to include thrombosis.

A disadvantage of injecting a liquid embolic agent into the endoleak sac is that the biocompatible polymer dissolves over time and is absorbed into the blood stream. A disadvantage of endovascular coiling is that aneurysms are often incompletely treated and carry a risk of aneurysm recurrence. In addition, coils are smaller in size to the aneurysm sac and may not fill the aneurysm sac completely.

United states patent application number US 2011/0054519 A1 in the name of Malte Neuss entitled "Device for closing defects in the vascular system" discloses a self-expanding device, particularly an implant, for closing defect openings in the human or animal body, which device, in a first state, has the shape of an elongated tube with slotted segments and in a second state has a shortened shape with formation of at least one open or substantially closed hollow structure of considerable transverse extent, where in the slotted segments of the tube form individual webs that are each connected to adjacent webs such that a net-like overall structure is obtained in the second state.

United States patent application number US 2011/0152993 A1 in the name of Sequent Medical Inc., entitled "Multiple layer filamentary devices or treatment of vascular defects" discloses devices and methods for treatment of a patient's vasculature with some embodiments configures for delivery with a microcatheter for treatment of the cerebral vasculature of a patient. Some embodiments may include a permeable shell and inner structure configured to occlude blood flow there-through.

OBJECT OF THE INVENTION

It is an object of this invention to provide an aneurysm occluder which, at least partially, alleviates some of the abovementioned difficulties.

SUMMARY OF THE INVENTION

In accordance with this invention there is provided an aneurysm occluder comprising a deformable housing and an absorber or material that causes blood clotting made of an absorbent material in and/or attached to the housing.

The absorber will expand, even to many times its size, and will then be supported by the deformable housing in that it would push on the inside of the housing as it expands.

The housing further includes a pressure sensor therein and/or attached thereto.

The housing may have the ability to bind and release specific drug substances that may either stimulate blood clotting or deliver other medicine.

The housing may be made of mesh.

There is provided for the absorber to be elongate or interwoven into the housing mesh.

Some or all of the weave threads of the mesh or of the weft threads of the woven mesh may include clotting agents or absorbent agents or both or a combination of both.

A still further feature of the invention provides for opposite ends of the absorber to be attached to the housing.

The pressure sensor is an implantable blood pressure sensor that is attached to the housing mesh.

The pressure sensor may communicate with a remote station through a wireless link. Specific markers will indicate the ends of the housing and the position of the pressure sensor. Other position markings may be included on the mesh or elsewhere on the occluder.

A yet further feature of the invention provides for the housings to include disc shaped inserts. A platinum elongate strip may also indicate (attached to housing) the precise positioning of the occluder and entire housing in whether constrained, deformed or shortened.

There is provided for the disc-shaped inserts to be made of polytetrafluoroethylene (PTFE).

The markers and platinum strip will be x-ray detectable.

The absorbent material (interwoven or elongated co-axial) may absorb many times it weight e.g. polyvinyl alcohol or gelatin sponge. It may therefore expand beyond the housing mesh or fill within the mesh to augment blood clotting, by forming a barrier to blood flow.

The sponge material may or may not disintegrate with time.

A third type of material may be included into the housing mesh: fiber strands or thrombin particles which interact with blood components (clotting cascade and platelets) and induce intrinsic clotting.

A further component of the housing mesh is to pharmacologically attach specific substances (drugs) to the mesh.

The drugs may perform specific functions either related to including blood clotting (e.g. calcium) or decreasing the size of the aneurysm (e.g. doxycycline) or decrease inflammation in the aneurysm wall e.g. dexamethasone or indometheon (e.g. anti-inflammatory drugs such as dexamethasone or indomethean). These drugs may have variable "election time" and be released into the aneurysm slowly over many months.

The inserts are membranes.

There is provided for the housing to have tubular shape with closed off ends, in an expanded or relaxed state. The deformable housing may be compressed or elongated in length and/or breadth, in three dimensions to adjust to the inner shape of the aneurysm cavity, in situ.

There is further provided for the housing to have memory wherein the housing tends to return to an expanded tubular state when unconstrained.

The mesh may be made of metal strands.

The metallic strands may be stainless steel or nickel titanium.

There is provided for the disc-shaped inserts to have a diameter similar to the diameter of the housing in its expanded state. The disc-shaped inserts may be positioned at opposite ends of the housing, and/or at various intervals there between, within the housing.

There is also provided for the disc-shaped inserts to be, at their circumference, secured to the housing so that the disc-shaped inserts face the longitudinal direction of the housing. Alternatively, or in addition, central locating holes in the disc-shaped inserts locate over the absorber.

The occluder includes an absorber, sponge which may also include or be made of or include Fibrin/trombone to enhance biologic clotting.

Medication or drugs may be included on the housing or mesh or elsewhere to enhance clotting or affect an aneurysm wall.

The occluder includes markers so that the position of the occluder, once implanted, could be determined. The markers may be strands or any other body attached to any part of the occluder to show the orientation, deformation of the occluder once implanted. The marker or markers will be used to indicate position, shape, deformed state etc. of the housing.

These and other features of the invention are described in more detail below.

BRIEF DESCRIPTION OF DRAWINGS

One embodiment of the invention is described below, by way of example only, and with reference to the accompanying drawings in which.

DETAILED DESCRIPTION OF THE DRAWINGS

Figure 1:
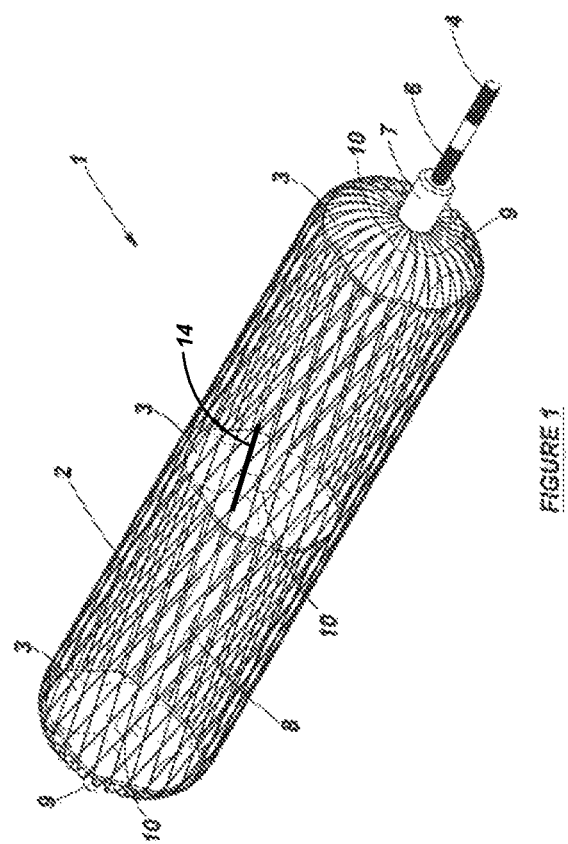
FIG. 1: is a perspective view of an aneurysm occluder in accordance with the present invention.

With reference 10 the drawings, an aneurysm occluder is generally indicated by reference numeral 1.

The aneurysm occluder 1 has a deformable housing 2 which consists of a plurality of metallic strands woven to form a deformable and compressible mesh. The strands may be stainless steel of nickel titanium. The mesh is tubular and has closed off ends to be generally sausage shaped in a relaxed position.

A marker or markers (not shown) of an elongate strand of platinum wire can be attached to the housing so that the position and deformation of the housing can be gleaned by x-ray or other means. It will be appreciated by those skilled in the art that many forms and shapes of markers could be attached to the housing, mesh or other parts of the occluder so that its position, deformation or shape can be gleaned using x-rays or other means.

The occluder 1 further has first securing means 6 which is located at a first end of the housing 2. The securing means, secures at its outer end 4, to an applicator's operational end, which would be an end of an guide wire in a catheter tube 11.

A plurality of disc-shaped inserts 3 is located within the housing 2 and may be secured to the housing 2. The plurality of disc-shaped inserts 3 are placed at least 2 centimeters apart and enhance the clotting function of the aneurysm occluder 1.

The housing and/or absorbent material and/or clotting material is biased to its relaxed tubular shape and may be compressed to take the shape of the inside of a catheter tube 11 or aneurysm sac 12 in which it is placed.

The disc-shaped inserts 3, which are circular in shape and made of a thin polytetraflouroethylene sheet or membrane, have a diameter similar to the housing 2, in cross-section, in an unconstrained state. In a preferred embodiment, there are three disc-shaped inserts 3 facing each other and spaced along the length of the housing 2, inside of the housing. It will, however, be appreciated that any amount may be used. Each disc-shaped insert 3 may, at its circumference, be secured to the mesh housing 2 by a fine strand.

An elongate absorber 8 protrudes through holes 10 at the center of each insert 3. The absorber may be attached to opposite ends 9 of the housing 2. The absorber extends axially inside the housing. The absorber is deformable and can be bent and deformed to fit into a cavity into which the occluder fits. The absorber is made of cellulose or other absorbent material. The absorber will increase in size whilst the housing does not. The absorber may be biodegradable. The absorber may be interwoven into the housing, be elongate within or be an extraneous piece (tail) that is carried by the housing. This material may be woven into the mesh and may even be some of the weft or weave strands.

A pressure sensor such as an implantable blood pressure sensor 7 is attached to the housing's first end. The blood pressure sensor includes a communication means for wireless communication with an interrogations mean to take blood pressure readings of the blood pressure at a point in the human or animal body where the sensor is located.

Figure 2:
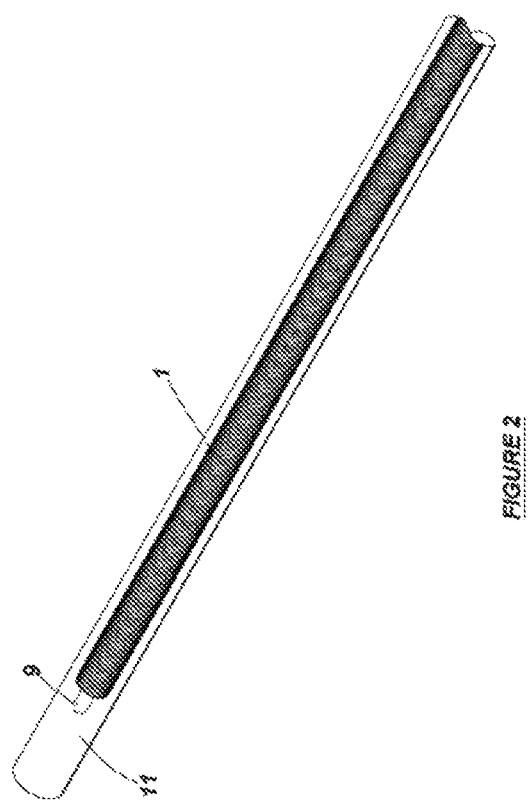
FIG. 2: is a perspective view of part of the occluder of FIG. 1 compressed in a catheter.
Figure 3:
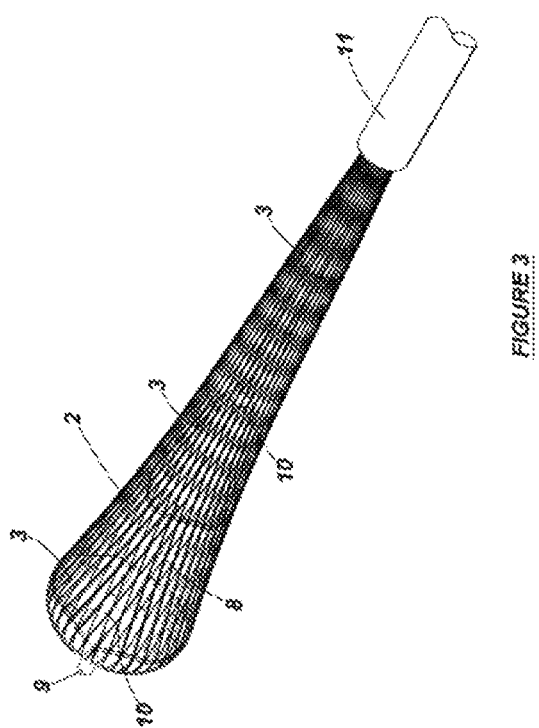
FIG. 3: is the same view as shown in FIG. 2 but with the occluder partly pushed out of the catheter.

In use, the occluder 1 is attached to the end of a guide wire, deformed and placed in a catheter tube as shown in FIG. 2. The deformation causes the disc-shaped inserts 3 to collapse onto the relatively thin, elongate absorber 8. The occluder 1 is then placed in the aneurysm cavity using the catheter as is known in the art. FIG. 3 shows the occluder being pushed out of the catheter so it can locate inside the aneurysm sac. The occluder is allowed to expand and fill the cavity taking up the shape of the cavity. The mesh housing 2 and disc-shaped inserts 3, and absorber 8 encourage blood clotting.

Figure 4:
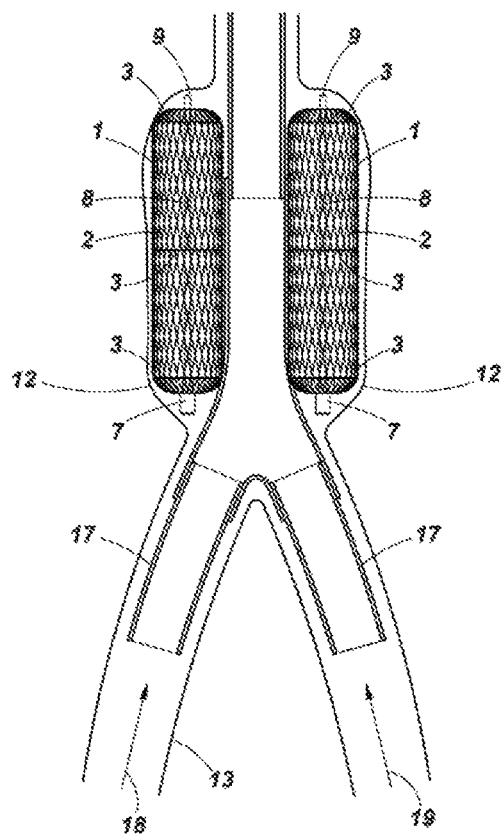
FIG. 4: shows two occluders inserted in an aneurysm cavity.

As shown in FIG. 4, two occluders are inserted in an aneurysm sac. This figure is only a diagrammatical representation. In practice the cavity would not be as symmetrical as shown and would deform the housing, inserts and absorber.

The insertion path could be along paths 18 or 19 of arteries 13, behind the stent extension 17, into the aneurysm sac 12.

This invention thus provides an aneurysm occluder which can fill or assist to fill the cavity of an aneurysm. It will be readily appreciated by persons skilled in the art that when the aneurysm occluder 1 is constrained in the aneurysm cavity, the housing, inserts and absorber slows or inhibits flow of blood and thus promotes thrombosis. The absorber 8 also absorbs blood and will swell when absorbing blood thus also enhancing thrombosis as it will inhibit blood flow in the cavity.

It will be appreciated that many variations are possible with the present embodiment according to the invention without departing from the scope of spirit of the invention. For example, instead of being circular in cross section, the housing may be square or rectangular in cross-section. The absorber and inserts may also take many forms and shapes.

The size of the current occluder may be increased many times within the body by addition of the absorber/sponge material. The sponge material also forms a barrier to blood flow and conforms to aneurysm sac.

The invention claimed is:

1. An aneurysm occluder comprising a housing and disc shaped inserts disposed in the housing, each disc shaped insert having a central locating hole located over an absorber or a blood-clotting material, the absorber or the blood-clotting material being made of an absorbent material in or attached to the housing, wherein the disc-shaped inserts are secured to the housing and remain at least 2 centimeters apart from one another while secured to the housing.

2. The occluder as claimed in claim 1 in which the absorber or the blood-clotting material will expand and will be supported by the deformable housing when it pushes on the inside of the housing as it expands.

3. The occluder as claimed in claim 1 in which the housing includes a pressure sensor therein and/or attached thereto.

4. The occluder as claimed in claim 3 in which the pressure sensor is an implantable blood pressure sensor that is attached to the housing mesh, and the pressure sensor communicates with a remote station through a wireless link.

5. The occluder as claimed in claim 1 in which the housing is made of mesh, and the absorber or the blood-clotting material is elongate or elongate and interwoven into the housing mesh.

6. The occluder as claimed in claim 5 in which some or all of the weave threads of the mesh and/or some or all of the weft threads of the woven mesh includes clotting agents or absorbent agents or both or a combination of both.

7. The occluder as claimed in claim 5 in which the absorbent material can absorb many times it weight and is made of and expands, when absorbing fluid, to fill the mesh housing and thus forming a barrier to blood flow.

8. The occluder as claimed in claim 7 in which the absorbent material disintegrates with time.

9. The occluder as claimed in claim 5 in which the mesh is made of metal strands which is stainless steel or nickel titanium.

10. The occluder as claimed in claim 1 in which a platinum elongate strip attached to housing indicates the precise positioning of the occluder and entire housing and whether constrained, deformed or shortened.

11. The occluder as claimed in claim 1 in which fiber strands or thrombin particles which interact with blood components are included in the mesh or forms part of the mesh.

12. The occluder as claimed in claim 11 in which the pharmacological substances are slow release substances and enhance blood clotting or decreases the size of the aneurysm or decrease inflammation in the aneurysm wall.

13. The occluder as claimed in claim 1 in which pharmacological substances are attached to the mesh.

14. The occluder as claimed in claim 1 in which the housing has a tubular shape with closed off ends, in an expanded or relaxed state and to be compressible or elongated in length and/or breadth, in three dimensions, to adjust to the inner shape of the aneurysm cavity, in situ.

15. The occluder as claimed in claim 1 in which the housing has memory so that the housing tends to return to an expanded tubular state when unconstrained.

16. The occluder as claimed in claim 1 in which the disc-shaped inserts have a diameter similar to the diameter of the housing in its expanded state.

17. The occluder as claimed in claim 1 in which the disc-shaped inserts are positioned at opposite ends of the housing, and at various intervals there between, within the housing.

18. The occluder as claimed in claim 1 in which the disc-shaped inserts are, at their circumference, secured to the housing so that the disc-shaped inserts face and are aligned with the longitudinal direction of the housing.

19. The occluder as claimed in claim 1 in which the absorber or the blood-clotting material extends between opposite ends of the housing and is located substantially centrally in the housing.

20. The occluder of claim 1, further comprising a pressure sensor, wherein at least two of the disc-shaped inserts are disposed proximal relative to the pressure sensor, and the pressure sensor is disposed proximal relative to an attachment point that secures to an applicator.

* * * * *